United States Patent
Lane et al.

(12)

(10) Patent No.: US 6,334,873 B1
(45) Date of Patent: Jan. 1, 2002

(54) HEART VALVE HAVING TISSUE RETENTION WITH ANCHORS AND AN OUTER SHEATH

(75) Inventors: Ernest Lane, Huntington Beach, CA (US); David Tompkins, Surrey; David Hemsley, Hertz, both of (GB)

(73) Assignee: Autogenics, Scotland (GB)

( * ) Notice: Subject to any disclaimer, the term of this patent is extended or adjusted under 35 U.S.C. 154(b) by 0 days.

(21) Appl. No.: 09/161,809

(22) Filed: Sep. 28, 1998

(51) Int. Cl.[7] .................................................. A61F 2/24
(52) U.S. Cl. ...................................... 623/2.14; 623/2.15
(58) Field of Search ............................... 623/2.12, 2.13, 623/2.14, 2.15, 2.16, 2.17, 2.18, 2.19, 2.42

(56) References Cited

U.S. PATENT DOCUMENTS

| | | |
|---|---|---|
| 2,822,819 A | 2/1958 | Geeraert |
| 3,548,418 A | 12/1970 | Angell et al. |

(List continued on next page.)

FOREIGN PATENT DOCUMENTS

| | | | | |
|---|---|---|---|---|
| EP | 0125393 A1 | * | 10/1981 | ................ 623/2.12 |
| EP | 0179562 A1 | * | 9/1985 | ................ 623/2.12 |
| EP | 0 179 562 A1 | | 4/1986 | |
| GB | 21136533 A | * | 8/1983 | ................ 623/2.12 |
| WO | WO 94/04099 | | 3/1994 | |

OTHER PUBLICATIONS

*Degenerative Calcification in Tissue Valves—A Metabolic/Hemodynamic and Immunologic Problem*, Love et al., Abstract Published for the First Scientific Meeting of the international Association for Cardiac Biological Implants, Chicago, Apr. 5, 1987.
*Dopler and Hemodynamic Characteristics of the Autogenics Bioprosthetic Valve*, Khan et al.
*Rapid Intraoperative Fabrication of an Autogenous Tissue Heart Value: A New Technique*, pp. 691–689, Love, et al., 1986.

(List continued on next page.)

*Primary Examiner*—David H. Willse
*Assistant Examiner*—Suzette J. Jackson
(74) *Attorney, Agent, or Firm*—Knobbe, Martens, Olson & Bear, LLP

(57) ABSTRACT

An apparatus and a method for constructing a heart valve prepared from autologous tissue. Three tissue leaflets are held in place with tissue anchors on a tissue mounting frame having an annular base and a plurality of commissure posts extending from the base. An elastomeric sheath rests gently on the tissue leaflets to prevent the leaflets from coming off of the anchor hooks and encloses the leaflets to form valve cusps. The leaflets touch each other on a coaptation line with an angle of approximately 65° relative to the commissure post. The heart valves can be constructed intraoperatively in a short time, typically ten minutes. The low coaptation angle and the fact that the leaflets are held in place without being clamped between two unyielding members minimize stress on the tissue.

22 Claims, 13 Drawing Sheets

U.S. PATENT DOCUMENTS

| | | | |
|---|---|---|---|
| 3,570,014 A | | 3/1971 | Hancock |
| 3,714,671 A | | 2/1973 | Edwards et al. |
| 3,744,062 A | | 7/1973 | Parsonnett |
| 3,755,823 A | | 9/1973 | Hancock |
| 3,983,581 A | | 10/1976 | Angell et al. |
| 4,035,849 A | | 7/1977 | Angell et al. |
| 4,079,468 A | | 3/1978 | Liotta et al. |
| 4,084,268 A | | 4/1978 | Ionescu et al. |
| 4,106,129 A | | 8/1978 | Carpentier et al. |
| 4,172,295 A | | 10/1979 | Batten |
| 4,192,020 A | | 3/1980 | Davis et al. |
| 4,247,292 A | | 1/1981 | Angell |
| 4,291,420 A | | 9/1981 | Reul |
| 4,297,749 A | | 11/1981 | Davis et al. |
| 4,388,735 A | | 6/1983 | Ionescu et al. |
| 4,470,157 A | | 9/1984 | Love |
| 4,490,859 A | | 1/1985 | Black et al. |
| 4,501,030 A | | 2/1985 | Lane |
| 4,605,407 A | | 8/1986 | Black et al. |
| 4,687,483 A | | 8/1987 | Fisher et al. |
| 4,692,164 A | | 9/1987 | Dzemeshkevich et al. |
| 4,725,274 A | | 2/1988 | Lane et al. |
| 4,851,000 A | | 7/1989 | Gupta |
| 5,037,434 A | | 8/1991 | Lane |
| 5,147,391 A | | 9/1992 | Lane |
| 5,163,955 A | | 11/1992 | Love et al. |
| 5,326,370 A | | 7/1994 | Love et al. |
| 5,326,371 A | | 7/1994 | Love et al. |
| 5,423,887 A | | 6/1995 | Love et al. |
| 5,489,298 A | | 2/1996 | Love et al. |
| 5,549,665 A | * | 8/1996 | Vesely et al. ............... 623/2.14 |
| 5,571,174 A | | 11/1996 | Love et al. |
| 5,571,567 A | * | 11/1996 | Shah ........................... 427/379 |
| 5,612,885 A | | 3/1997 | Love |
| 5,653,749 A | | 8/1997 | Love et al. |
| 5,662,705 A | * | 9/1997 | Love et al. ................. 623/2.12 |
| 5,755,782 A | | 5/1998 | Love et al. |
| 5,843,181 A | * | 12/1998 | Jaffe et al. .................. 623/2.12 |
| 5,855,601 A | * | 1/1999 | Bessler et al. .............. 623/2.12 |
| 5,928,281 A | * | 7/1999 | Huynh et al. ............... 623/2.12 |
| 5,935,163 A | * | 8/1999 | Gabbay ....................... 623/2.14 |
| 6,095,968 A | * | 8/2000 | Snyders ......................... 600/16 |
| 6,102,944 A | * | 8/2000 | Huynh et al. ............... 623/2.14 |
| 6,126,686 A | * | 10/2000 | Badylak et al. ............ 623/1.24 |
| 6,254,636 B1 | * | 7/2001 | Peredo ....................... 623/2.15 |

OTHER PUBLICATIONS

Experimental Evaluation of an Autologous Tissue Heart Valve, pp. 232–24, Love et al., J Heart Valve Dis. vol. 1, No. 2, 1992.

A construction technique for minimising valve leaflet fitigue failure in pericardial valves, Life Support Systems, Black, et al., Sep. 1984, Proceedings XI Annual Meeting ESAO, vol. 2 Supplement 1.

A fascia lata mitral valve based on the 'frustum' principle, Thorax, 1971, pp. 284–287, Brownlee and Yates.

Editorial Towards Understanding the Pericardium as Valve Substitute, pp. 213–15, Frater and Bodnar, The Journal of Heart Valve Disease 1992.

The flexible stent A new concept in the fabrication of tissue heart valve prostheses, The Journal Of Thoracic And Cardiovascular Surgery, vol. 62, No. 5, pp. 683–689; 693–695, Nov., 1971.

In Vitro Testing of Bioprostheses, vol. XXXIV Trans Am Soc Artif Intern Organs 1988, Reul et al., pp. 1033–1039.

A Method For Preparing And Inserting A Homograft Aortic Valve, The British Journal Of Surgery, B.G. Barratt–Boyes, pp. 847–856.

Replacement of heart valves with frame–mounted tissue grafts, Ionescu et al., Thorax 1974, pp. 56–67.

Frame–mounted tissue heart valves: technique of construction, Bartek, et al., Thorax 1974, pp. 51–55.

An Alternate Method for Applying a Dacron Cover to a Delrin Bioprosthetic Heart Valve Stent, C.S. Love, Biomedical Engineering III Recent Developments, Proceedings of the Third Southern Biomedical Engineering Conference, pp. 30–37.

The Autogenous Tissue Heart Valve: Experience with Pericardium, Love et al. , Pericardial Tissue as a Cardiac Valve Substitute, Proceedings of a Symposium, Sep. 1988.

A fascial Frustum valve for aortic valve replacement, Yates, Thorax 1971, pp. 184–189.

* cited by examiner

HEART VALVE HAVING TISSUE RETENTION WITH ANCHORS AND AN OUTER SHEATH

FIELD OF THE INVENTION

This invention relates to improvements in heart valves using autologous tissue held in place by anchors and an outer sheath. The heart valve can be constructed intraoperatively within a short time, typically 10 minutes.

BACKGROUND OF THE INVENTION

Several types of heart valves are presently available for use in replacing diseased or malfunctioning heart valves in humans.

One form of heart valve is constructed from animal tissue, typically from bovine or porcine aortic valve tissue. These valves must typically be constructed in a laboratory well in advance of when they will be needed and then stored in an aldehyde solution. Skilled technicians are required to assemble these valves. The valves constructed from animal tissue have relatively short lifetimes. The short lifetimes are caused by two factors. First, there is an antigenic reaction by the body to the animal tissue which causes the tissue to calcify, making it inflexible and more susceptible to failure with time. Second, the tissue is often stored in glutaraldehyde before implantation to try to decrease the antigenic reaction. The aldehyde tends to tan the tissue to a leather-like consistency, which makes it wear out from the repeated stress of opening and closing.

Thus, although these animal tissue valves are widely used, most have to be replaced after about five to ten years. Replacing the valves poses risks to the patient, because a second open heart operation is then needed, with the attendant possibility of problems during the operation.

Mechanical heart valves are also available. These valves are made from hard, non-biological materials such as metals or ceramics. Although the mechanical heart valves are durable, the hard, non-biological surfaces on the valves tend to cause blood clots. The blood clots can cause heart attacks or strokes, and, as a result, patients with mechanical heart valves must take anticoagulant drugs. These drugs can lead to hemorrhagic complications. Also, patients on these drugs require frequent and lifelong laboratory tests of their clotting time.

Another type of heart valve, the autogenous tissue valve, is constructed with the patient's own tissue. A number of patents for autologous tissue heart valves and methods of making autologous tissue heart valves have issued to Autogenics, assignee of this application, including U.S. Pat. Nos. 5,161,955 and 5,326,371.

SUMMARY OF THE INVENTION

This invention provides an improved apparatus and method for constructing an autologous tissue heart valve. A significant factor of the invention is that both the configuration of the autologous tissue and its means for attachment to the frame of the valve prevent deleterious stress on the tissue.

Accurate placement of the autologous tissue is provided by forming pericardium tissue taken from the patient into three separate tissue leaflets, each generally semi-circular shape and having a plurality of tissue anchor holes located along a tissue cusp line. The location of these tissue anchor holes correspond to tissue anchor hooks permanently attached to a tissue mounting frame.

These three leaves of tissue are placed sequentially on the tissue anchor hooks of the tissue mounting frame so as to be located completely around the circumference of the tissue mounting frame. An elastomeric sheath is stretched over the exterior of the tissue mounting frame. This sheath prevents the tissue from coming off the tissue anchor hooks and rests gently on the tissue around the cusp line such that the tissue forms a naturally closed valve.

A significant feature of this invention is that the manner in which the autologous tissue is supported prevents deleterious stress on the tissue. The tissue is thus not clamped between two unyielding members, but rather supported and retained by the combination of anchors mated in tissue anchor holes and the elastomeric sheath engaging a peripheral portion of the tissue leaflets between the elastomeric sheath member and the inner tissue mounting frame.

Another feature of the invention is that the tissue leaflets are formed to include sufficient extra tissue area to provide a physiologically representative coaptation line angle to thereby reduce the stretch in the tissue held in place by the sheath and thus further reduce the stress in the tissue.

DETAILED DESCRIPTION OF THE INVENTION

Figure 1:
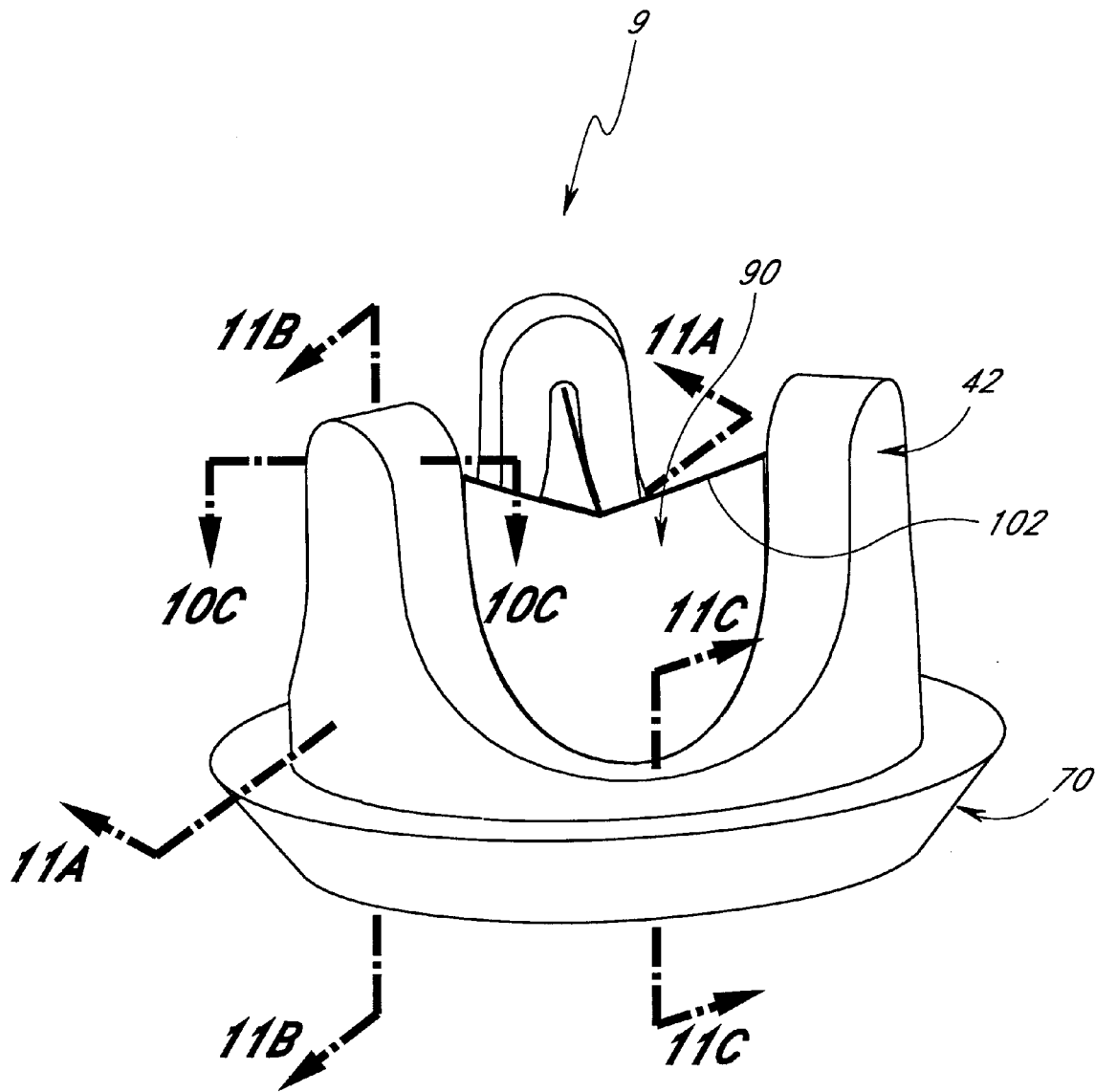
FIG. 1 is a perspective view of a preferred embodiment of an assembled autologous heart valve constructed in accordance with this invention.
Figure 3A:
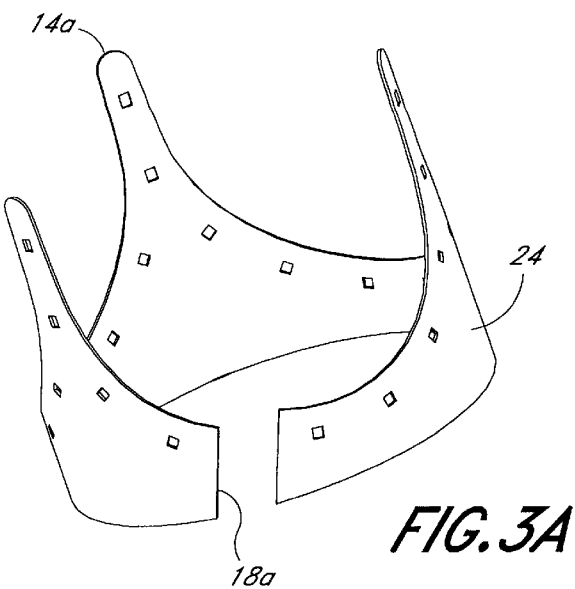
FIG. 3A is a perspective view of the outer frame after it has been rolled into a cylindrical configuration.
Figure 3B:
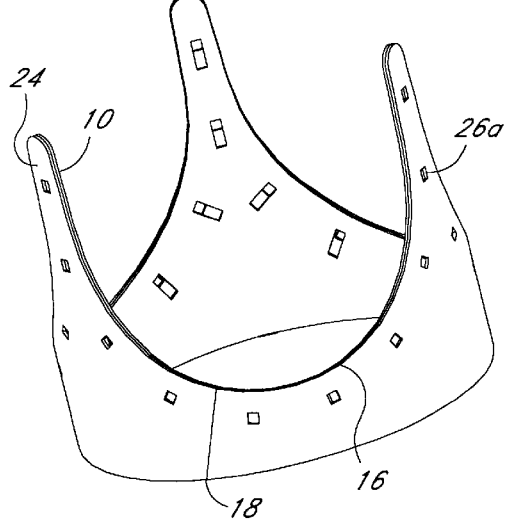
FIG. 3B is a perspective view of the inner and outer frames concentrically joined together.
Figure 3C:
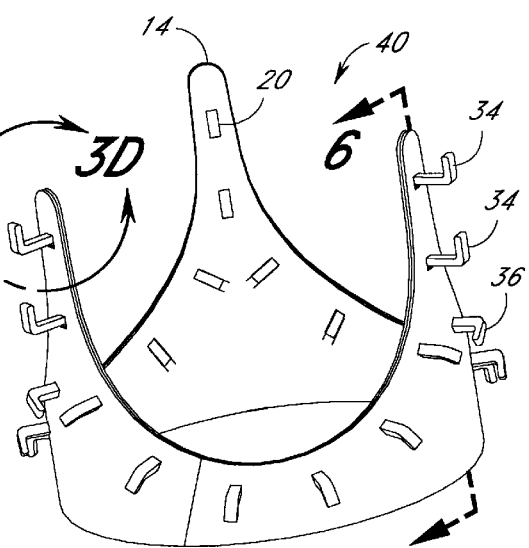
FIG. 3C is a perspective of the completed tissue mounting frame with tissue anchors before it is covered with cloth.
Figure 7A:
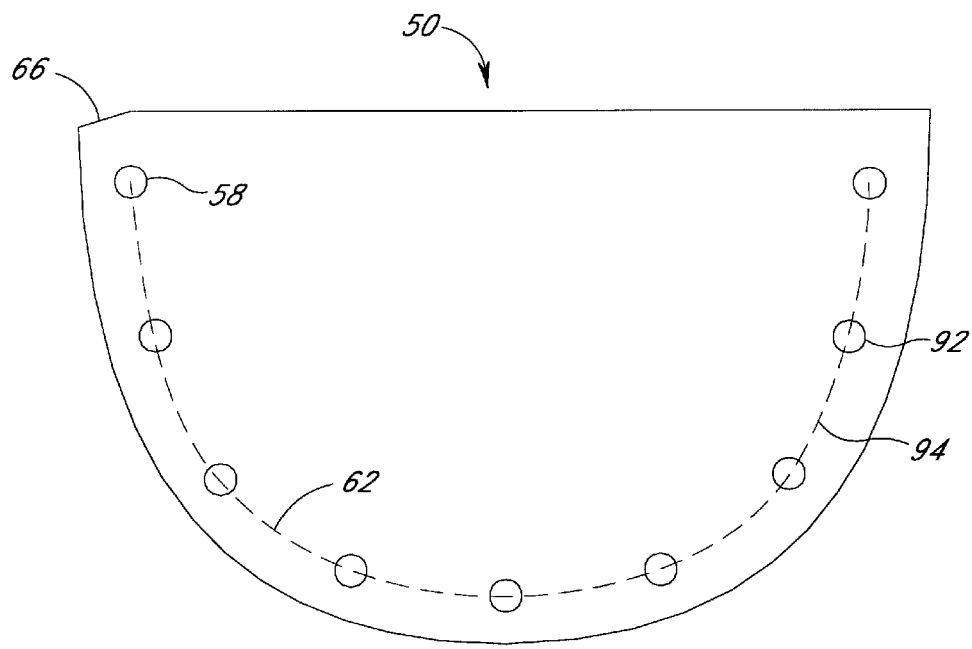
FIG. 7A is a front view of one of the autologous tissue leaflets.

FIG. 1 illustrates the preferred embodiment of the assembled autologous tissue heart valve 9 of this invention. This valve uses the patient's own tissue and is constructed intraoperatively from several factory manufactured components. Referring to FIGS. 3C and 7A, these components include a tissue mounting frame 40 (FIG. 3C) having a plurality of tissue anchor hooks 34 and 36. This tissue mounting frame 40 mounts three individual autologous tissue leaflets 50, one such leaflet being shown in FIG. 7A. The final assembled configuration of the three leaflets is shown at 90 in FIG. 1. An elastomeric outer sheath 42 covers the tissue mounting frame and assists in holding the tissue in place on the frame without placing undue stress on the tissue leaflets. An annular sewing ring 70 is mounted at the base of the tissue mounting frame and elastomeric sheath and used in the conventional manner to hold the assembled valve 9 in place within the patient's heart. As described below, this valve is designed to be intraoperatively assembled by the surgeon during the open heart procedure. Typical assembly times are of the order of 10 minutes.

Tissue Mounting Frame 40

Figure 2A:
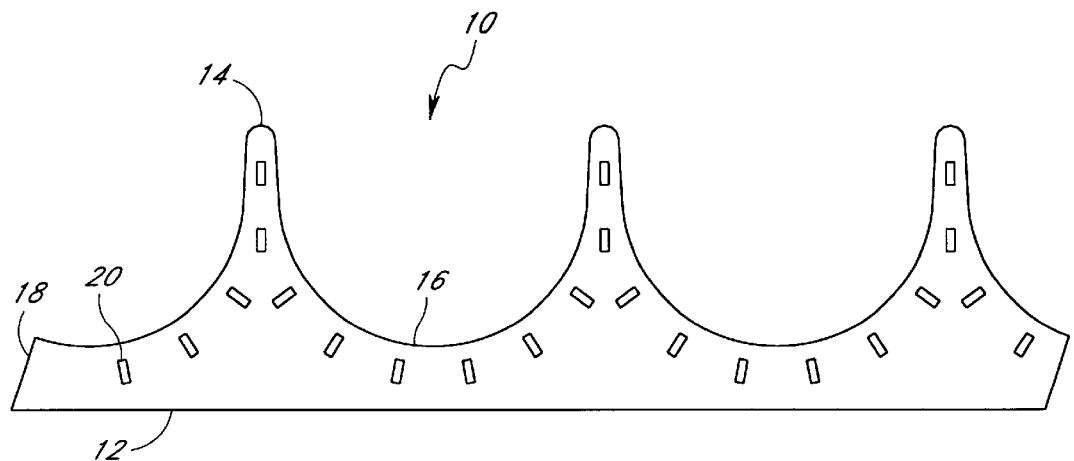
FIG. 2A is a front view during manufacture of the inner frame portion of the tissue mounting frame.

The components of tissue mounting frame 40 are shown in FIGS. 2A, 2B, 3A, 3B, 3C, 3D, 4 and 5. Shown in FIG. 2A is the inner frame 10 preferably manufactured with a base 12 having three commissure posts 14 extending from the base. In the constructed valve shown in FIG. 1, these commissure posts 14 are located along the axis of the valve in the direction of blood flow through the valve. Preferably, the three commissure posts 14 are spaced uniformly along the inner frame so that when the inner frame is assembled, the three commissure posts are separated by 120 degrees. The posts are preferably connected with scalloped walls 16 and the ends 18 of the inner frame are preferably slanted at an angle rather than being perpendicular to the base 12. A plurality of inner frame holes 20 are located along the perimeter of the scalloped walls 16 and commissure posts 14.

The inner frame 10 may be made of a variety of materials suitable for in vivo use, including certain metals and plastics. Metal is generally preferred over plastic as a material of construction, and ELGILOY is an especially preferred metal for fabricating the inner frame 10. DELRIN is an especially preferred plastic.

Figure 2B:
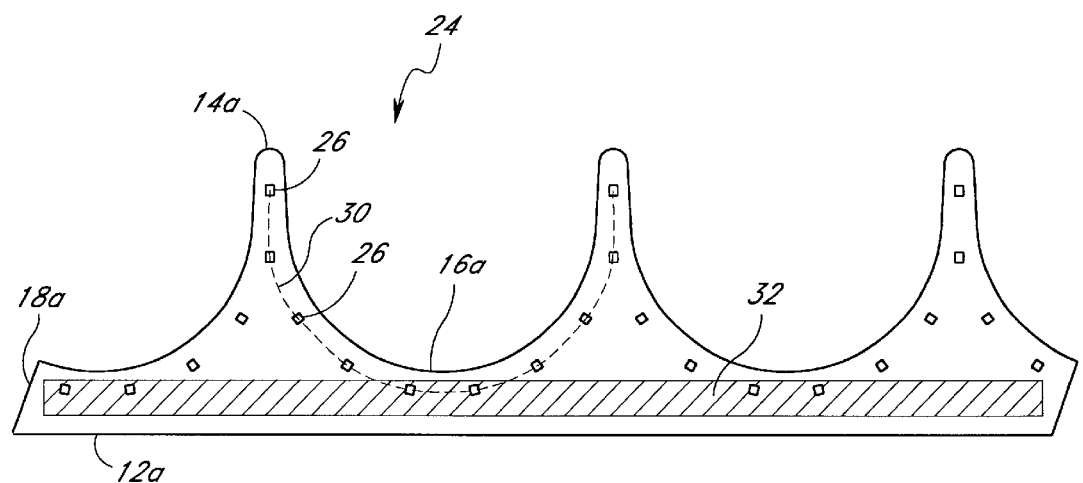
FIG. 2B is a front view during manufacture of the outer frame portion of the tissue mounting frame.

FIG. 2B shows the outer frame 24 portion of the tissue mounting frame 40. The outer frame, just as the inner frame, is constructed with a base 12a with a plurality of commissure posts 14a connected by a scalloped walls 16a. The ends 18a of the outer frame are also preferably slanted. A plurality of outer frame holes 26 are located along a cusp line 30, shown as a dashed line in FIG. 2B. This cusp line 30 is located close to the perimeter of the scalloped walls 16a and commissure posts 14a. The number of inner outer frame holes depend on the size of the valve but are generally in the range of 21 to 24. As described below, the outer frame holes are formed to be juxtaposed with the corresponding inner frame holes when the inner and outer frames are assembled together. The outer frame can also be made of a variety of materials including certain metals and plastics. ELGILOY is especially preferred.

The general location of a weld area 32 is shown on FIG. 2B with cross hatching. This weld area generally defines the area on the inner surface of the outer frame 24 which is later welded to the outer surface of the inner frame 10 to permanently bind the two frames together.

The inner frame 10 and outer frame 24 are rolled to form a cylindrical configuration. The appearance of the two cylindrically shaped members are quite similar so that only the outer frame 24 is shown in FIG. 3A. The two members 10 and 24 are then placed concentrically together and spot welded in the weld area 32 around the base 12 to form the structure shown in FIG. 3B. The frame ends 18 and 18a are placed 120 degrees apart when the two frames are welded together.

Figure 4:
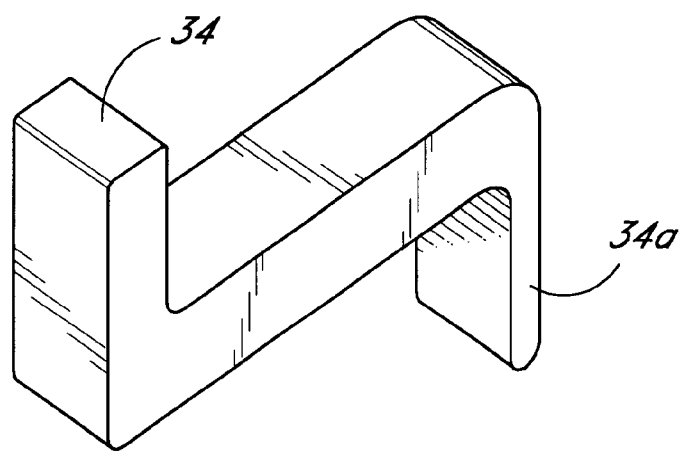
FIG. 4 is an enlarged view of the commissure tissue anchors.
Figure 5:
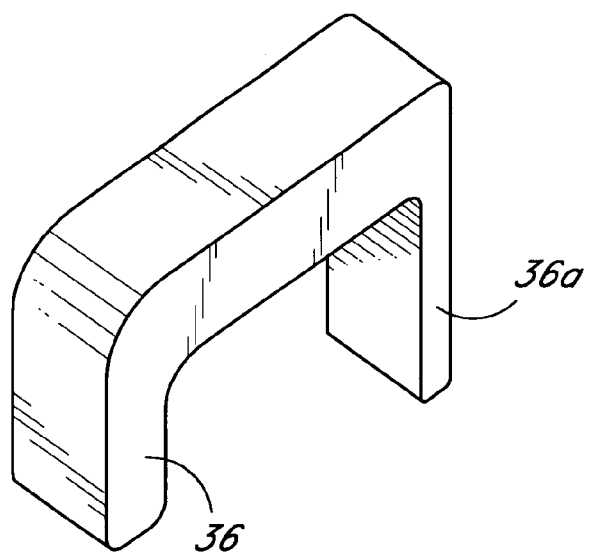
FIG. 5 is an enlarged view of the cusp tissue anchor.
Figure 6:
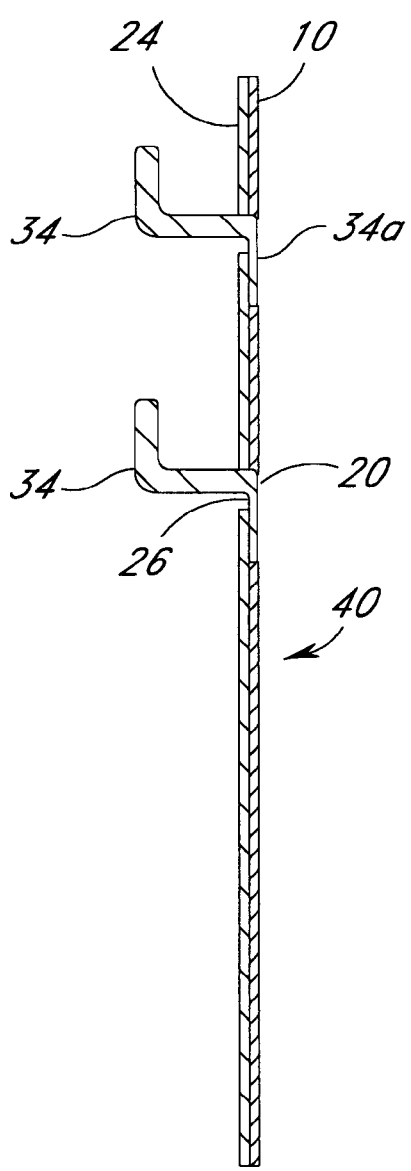
FIG. 6 is a cross-sectional view taken along line 6—6 of FIG. 3C.

Commissure post anchors 34 (FIG. 4) and cusp line anchors 36 (FIG. 5) are fabricated from metal, preferably ELGILOY. These anchors 34, 36 each include hook portions and a tang portion (34a and 36a), the latter being used to permanently attach the anchors to the tissue mounting frame 40. The hook portions are inserted from within the cylinder of the joined inner and outer frames through the inner frame holes 20 and outer frame holes 26 so that the hook portion extends outside of the surface of the outer frame (as shown in FIG. 3C and 3B). The tang portion 36a is spot welded to the inner surface of the outer frame 24 through the corresponding larger inner frame hole 20 located in the inner frame 10. As best shown in FIG. 6, the tang portion 34a abuts the inner surface of the outer frame 24 and resides within the corresponding larger inner frame hole 20. As shown in FIGS. 4 and 5, and as will become clear below, the commissure post anchors 34 are slightly longer than the cusp line anchors 36, because they hold two layers of tissue rather than one layer for the cusp line anchors.

Figure 3D:
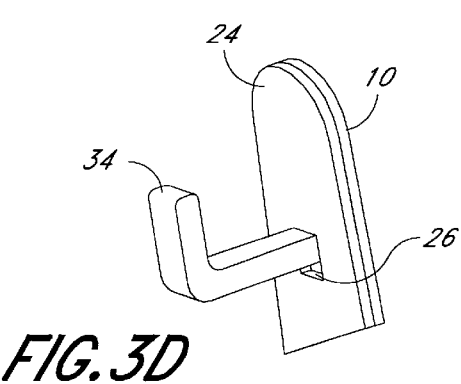
FIG. 3D is an enlarged perspective view showing one of the commissure post anchors.

FIG. 3D shows a more detailed view of the commissure post anchors 34 which extend through the outer frame hole 26 in the outer frame 24. The tang portion of the commissure post anchor 34 is spot welded to the inner wall of the outer frame 24 through the larger inner frame hole 20 (not shown) of the inner frame 10.

As shown in FIGS. 3C, 3D, and 6, the hook portions on the commissure post anchors 34 point upwardly, while FIG. 3C shows that the hook portions of the cusp line anchors 36 point away and downwardly from the cusp line 30. Normally, but not necessarily, there are two commissure post anchors 34 on each commissure post 14.

The tissue mounting frame 40 is manufactured in several sizes to suit the particular needs of the patient after the surgeon has removed the patient's valve during open heart surgery. Typical sizes in current use include 19, 21, 23 and 25 mm valves. The number of cusp line anchors vary, depending on the size of the tissue mounting frame. Normally, there are 6 commissure post anchors (2 per post) and 15–18 cusp line anchors per valve. The number of cusp line anchors depends on the size of the valve.

FIG. 6 shows a cross-sectional view of one side of the assembled tissue mounting frame 40 showing the inner frame 10, outer frame 24, and commissure post anchors 34. The two commissure post anchors 34 are welded to the inner wall of the outer frame 24 through the inner frame holes 20. Although not shown, the cusp line anchors 34 are similarly welded to the lower part of the frame 40.

Figure 11A:
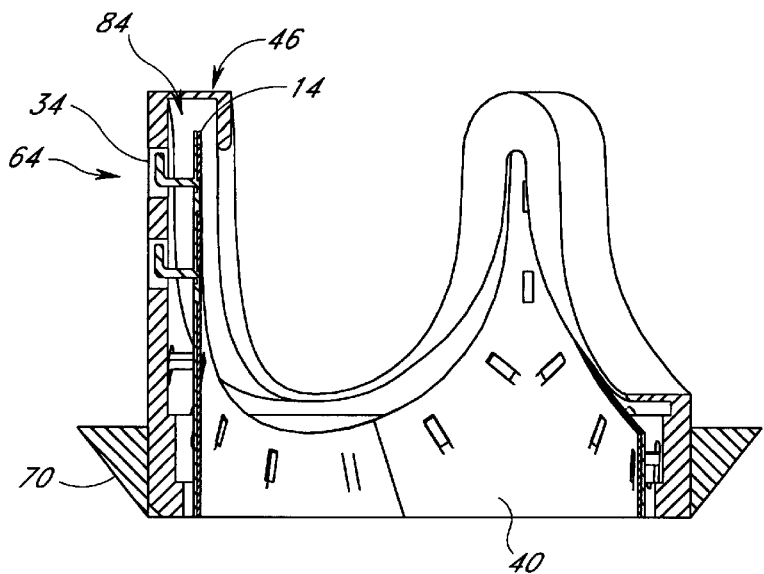
FIG. 11A is a sectional view taken along line 11A—11A of FIG. 1.
Figure 11B:
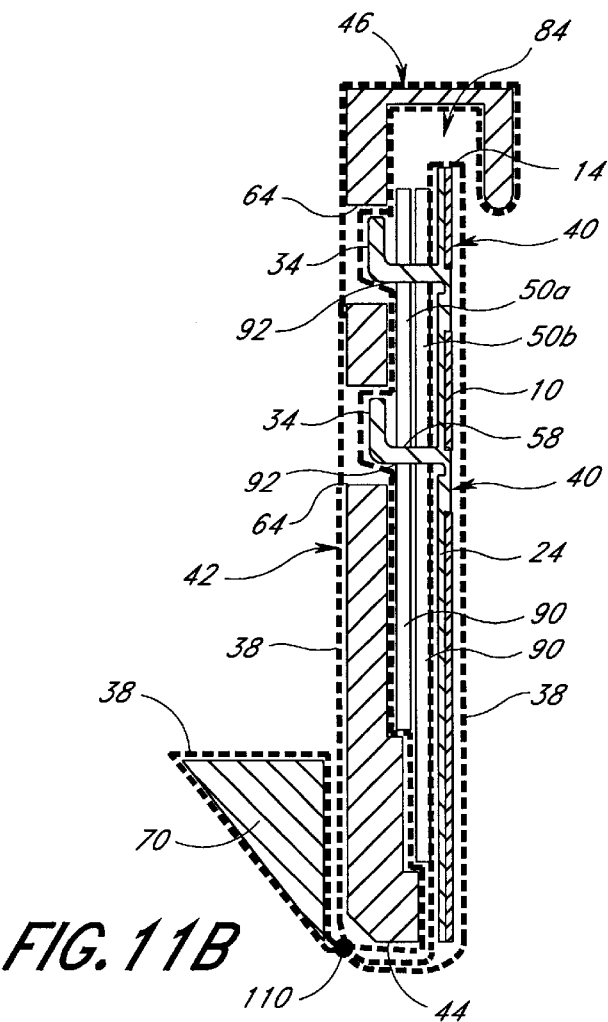
FIG. 11B is a cross-sectional view of line 11B—11B of FIG. 1.

After the inner frame 10, outer frame 24, commissure post anchors 34, and cusp line anchors 36 have been assembled and welded together, the assembled tissue mounting frame 40 is covered on both sides with DACRON cloth 38 (see FIG. 11B). DACRON is the trademarked name registered to DuPont for polyethylene terephthalate.

Figure 10A:
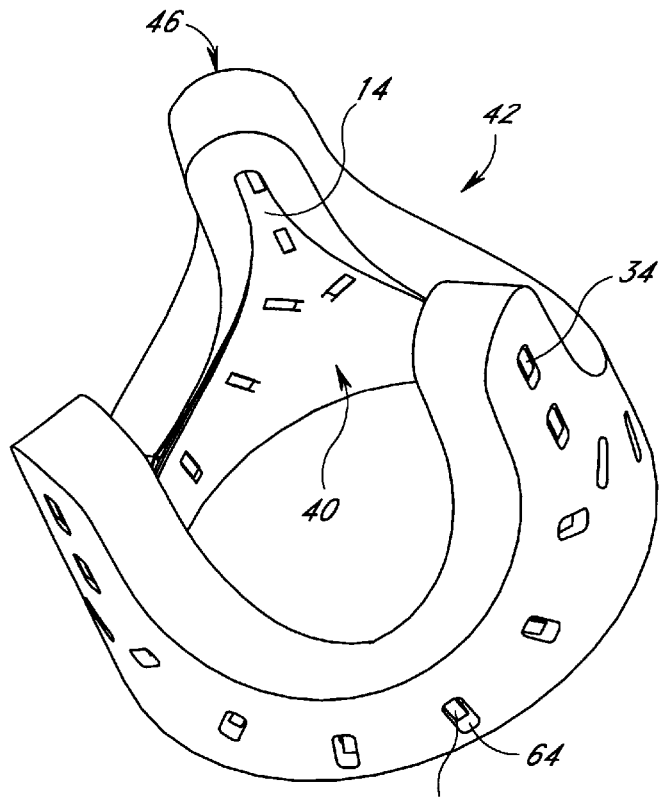
FIG. 10A is a perspective view of the elastomeric sheath attached to the tissue mounting frame.
Figure 10B:
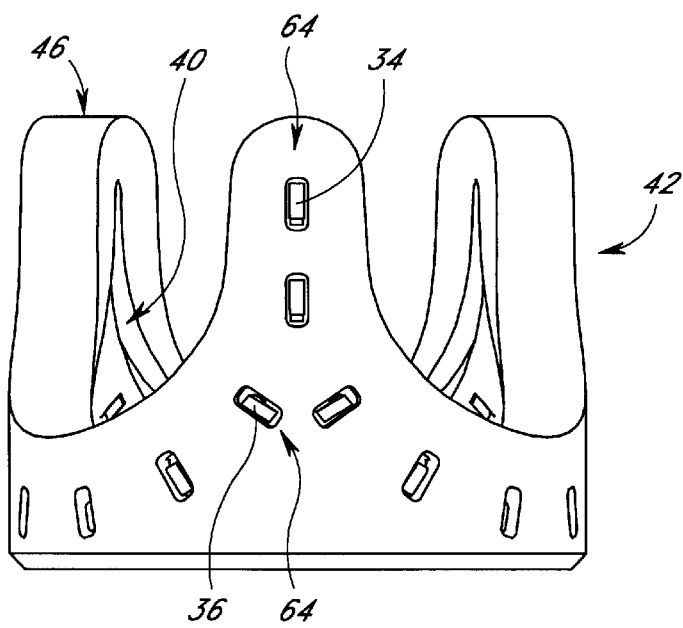
FIG. 10B is a front view of the elastomeric sheath shown in FIG. 10A.
Figure 10C:
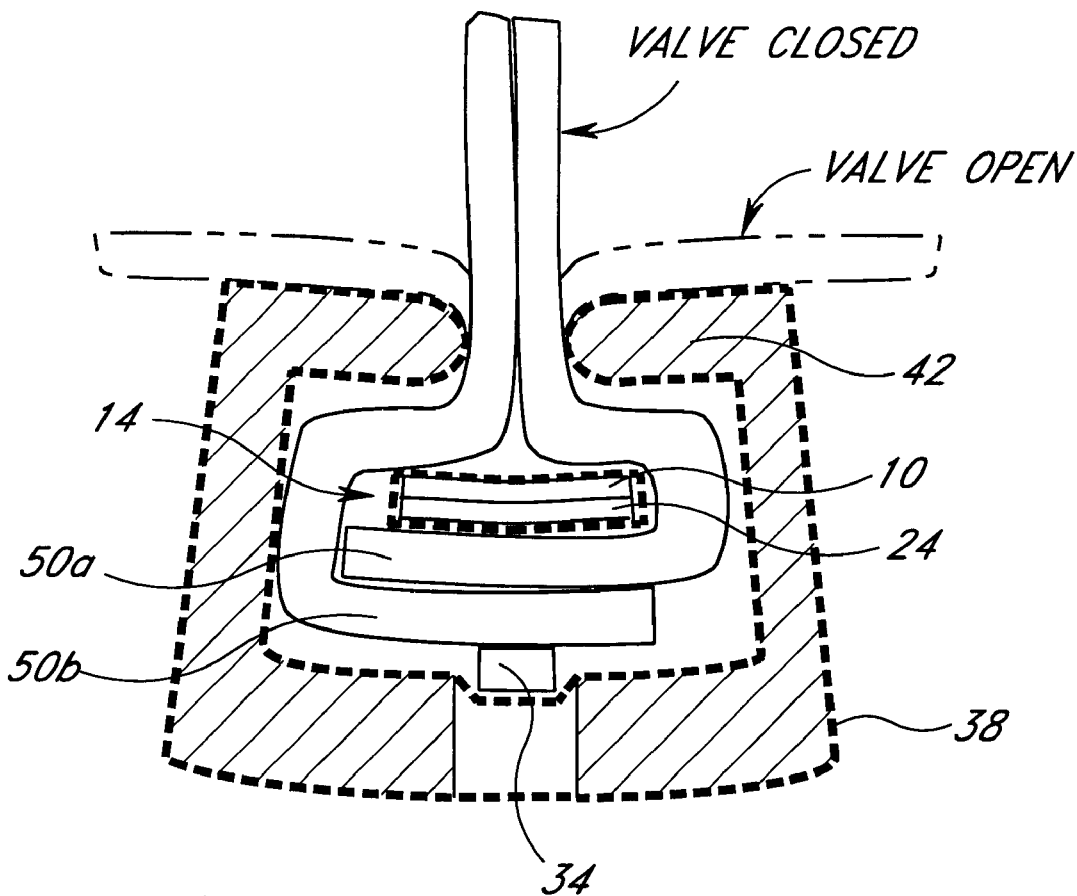
FIG. 10C is a sectional view taken along line 10C—10C of FIG. 1.
Figure 11C:
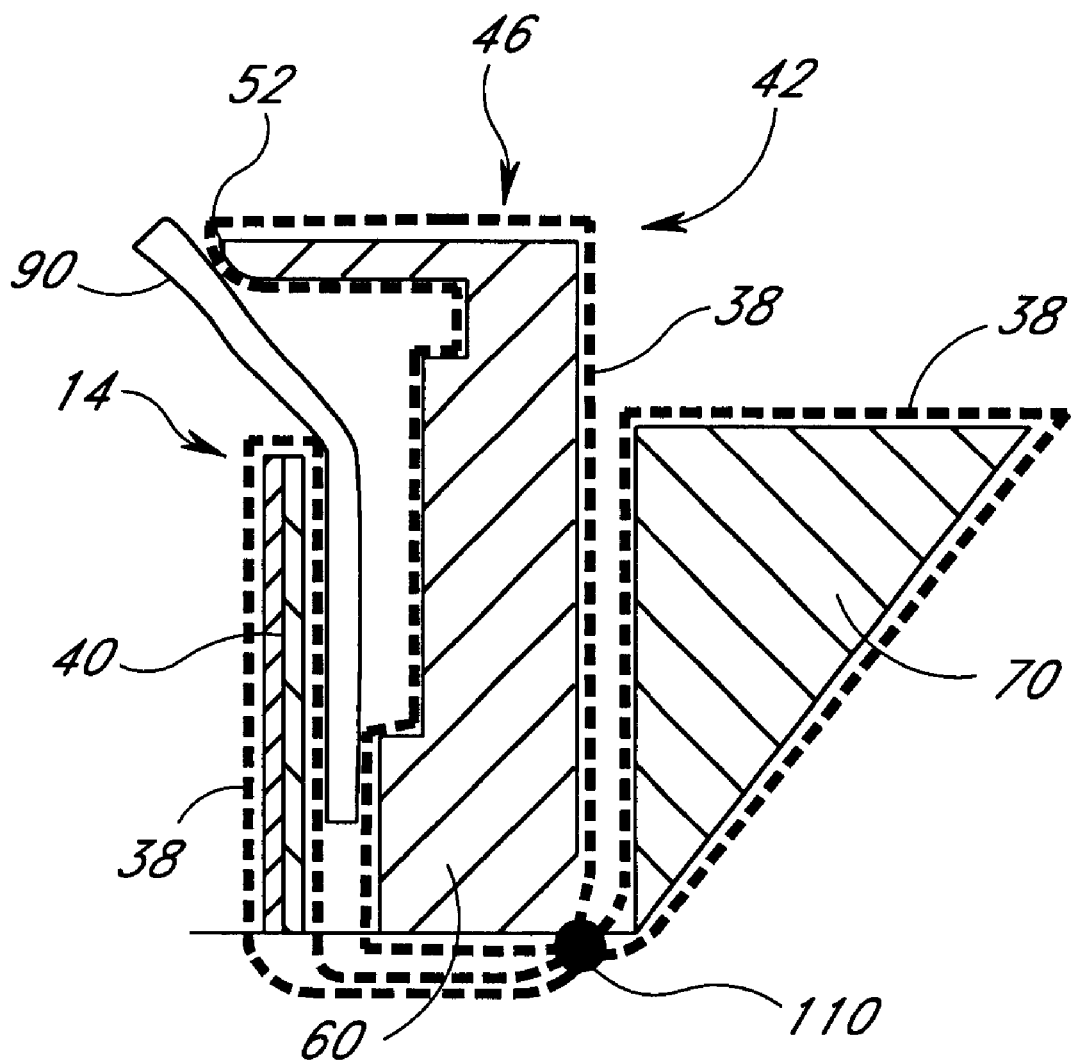
FIG. 11C is a cross-sectional view of line 11C—11C of FIG. 1.
Figure 12A:
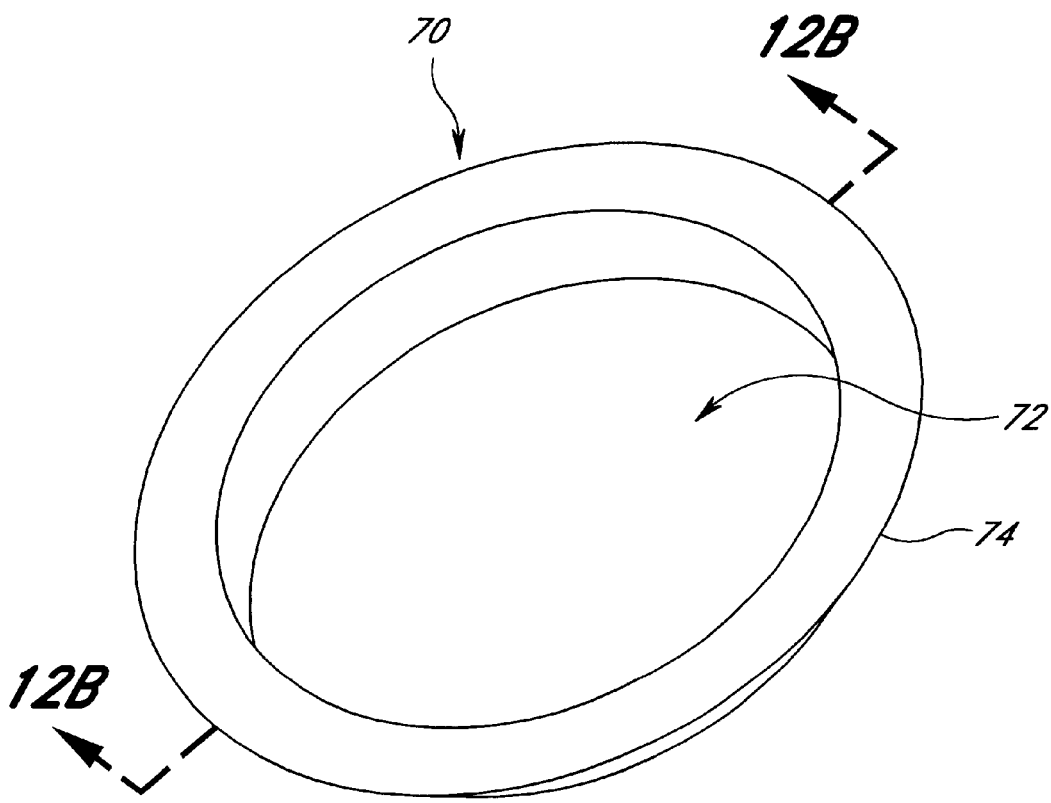
FIG. 12A is a perspective view of the annular sewing ring before it is covered with cloth.
Figure 12B:
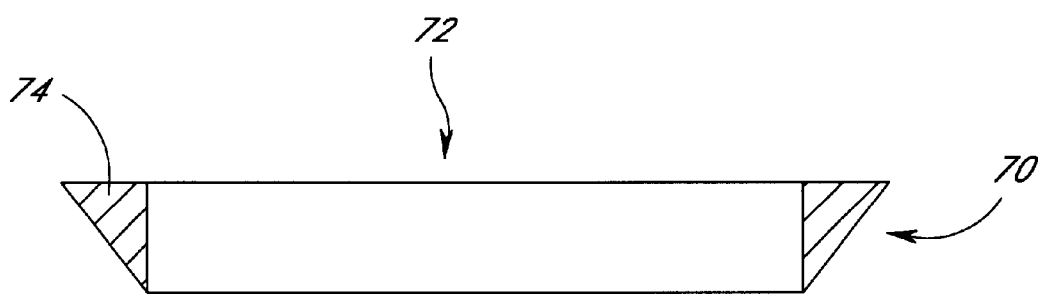
FIG. 12B is a cross-sectional view taken along line 12B—12B of FIG. 12A.

Since it is difficult to illustrate the cloth in the drawings, certain of the cross-sectional views, FIGS. 10C, 11B, 11C, show DACRON cloth 38 as a broken line 38 over the mounting frame 40 as well as the sheath 42 and sewing ring 70, described below. The commissure post anchors 34 and cusp line anchors 36 extend through the DACRON. As noted above, the spot welded anchors are nearly flush with and only slightly protrude (typically 0.003 inches) above the inner surface of the inner frame. As a result, when the frame is covered with DACRON, the inside surface is smooth, except for the knitted surface of the DACRON. Covering the frame with DACRON isolates the non-biological material, such as the metal of the frame, from the body. It also accomplishes the purpose of promoting tissue ingrowth into the interstices of the fabric, to further isolate the non-biological material from the body and integrate the valve into the heart. This helps avoid the problem of thromboembolism. Additionally, it provides a gentle interface between the metal and plastic components of the valve and the tissue and helps to nurture the tissue and promote its viability by allowing free passage of blood to the tissue.

Although the DACRON cover for the frame can be prepared in a variety of ways, one advantageous method was described in U.S. Pat. No. 5,163,955, herein incorporated by reference. A three-fingered DACRON sock or glove is described and shown in FIG. 4A of the patent. The three-fingered sock is formed by heat seaming sections of DACRON fabric together utilizing either hot wire, hot soldering iron, or ultrasonic techniques. Alternatively, the entire glove can be woven or knitted as one piece. The glove is then turned inside out (to remove the seam from the blood stream) pulled over the tissue frame and secured with a heat seam at the base of the glove. Similar fabrication methods can be used for the other DACRON coverings described herein.

Autologous Tissue Leaflets

Figure 8:
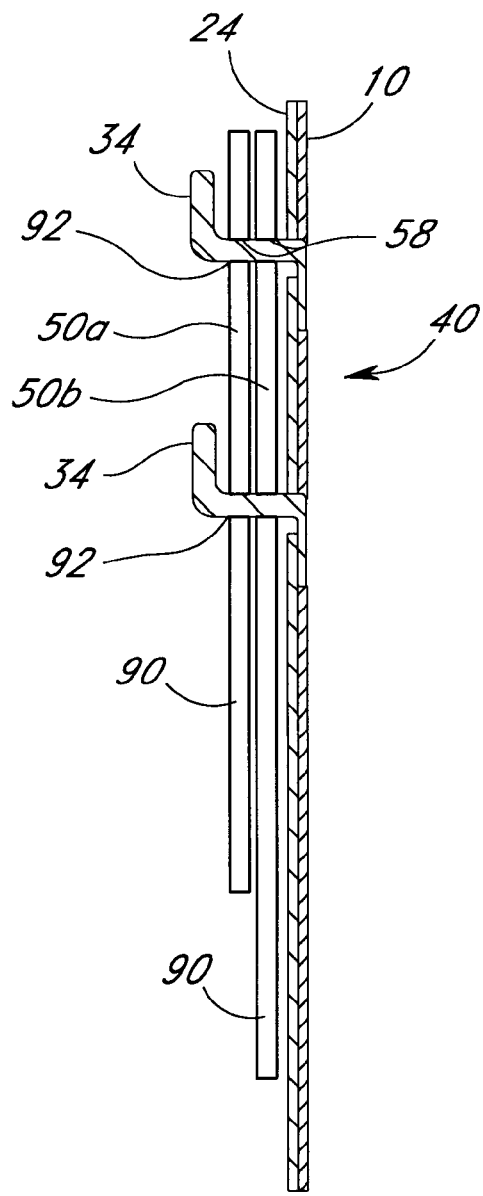
FIG. 8 is the cross-sectional view of FIG. 6 with the addition of two overlapping autologous tissue leaflets.

The autologous tissue leaflets 50 have a roughly semicircular shape as shown in FIG. 7A. Details of these leaflets, including the manner in which they are formed, is provided below. These tissue leaflets 50 are formed with a plurality of tissue anchoring holes 58 located along a tissue cusp line 62, shown as a dashed line on FIG. 7A. A tissue leaflet chamfer 66 is preferably cut in one corner to identify which leaflet is to be placed on top and overlap a portion of the preceding leaflet. During the intraoperative construction of the valve, these tissue holes 58 are fitted over the commissure post anchors 34 and cusp line anchors 36 to properly position the tissue leaflets to the assembled tissue frame. The attachment of the tissue leaflets 50 to the commissure post anchors is shown in FIG. 8. As shown, overlapping tissue leaflets 50a and 50b are attached to the tissue mounting frame 40 by having the tissue anchoring holes 58 inserted over the hook portions of the commissure post anchors 34. As a result, two layers of tissue leaflets 50 are attached to each of the commissure post anchors 34. However, only one tissue leaflet is present in the lower part of the frame where the leaflets do not overlap. The cusp line anchors 36 (not shown in its FIG. 8) have a hook portion that does not extend as far out from the frame 40.

Elastomeric Sheath

Figure 9A:
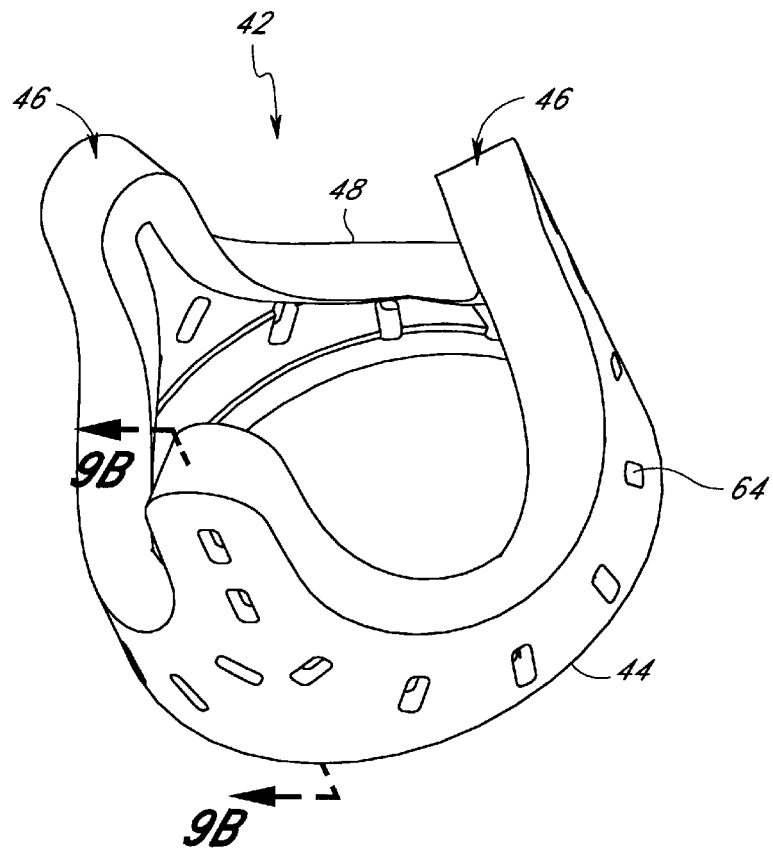
FIG. 9A is a perspective view of the elastomeric sheath.

The elastomeric sheath 42 is shown in FIG. 9A. This elastomeric sheath has a generally similar shape to that of the tissue mounting frame 40, with an annular elastomeric sheath base 44 and three elastomeric sheath commissure posts 46 extending from the base. The elastomeric sheath commissure posts 46 are connected with elastomeric sheath scalloped walls 48. A plurality of elastomeric sheath holes 64 correspond in position and number to those of the commissure post anchors 34 and the cusp line anchors 36 on the frame 40. The elastomeric sheath 42 is preferably made from silicone rubber covered on both sides with DACRON cloth.

Figure 9B:
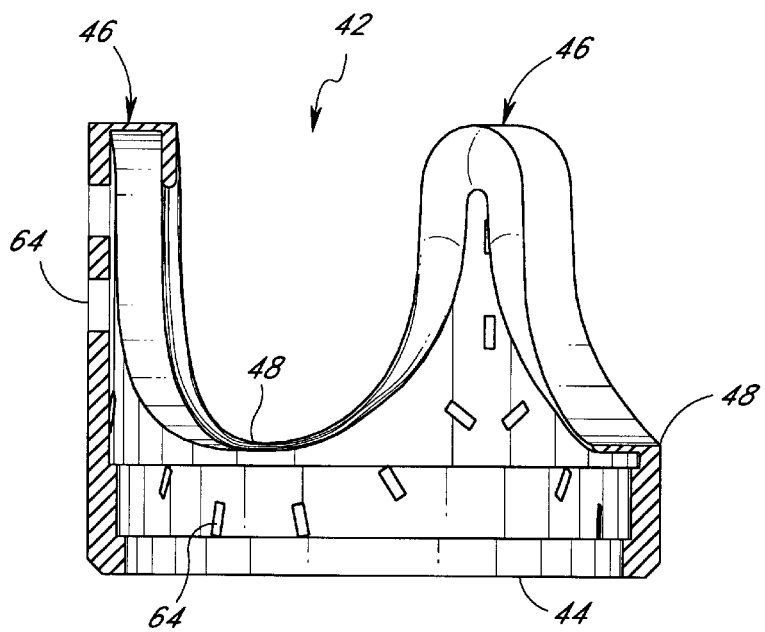
FIG. 9B is a cross-sectional view taken along line 9B—9B of FIG. 9A.

Additional views of the elastomeric sheath 42 are shown in FIGS. 9A, 10A, 10B, 10C, 11A and 11B. Please note that the FIGS. 10A, 10B and 11A are for illustrative purposes only since the sheath is shown in these figures attached to the frame 40 without the autologous leaflets 50. Such would not occur during construction of the valve since these leaflets would be first attached to the tissue mounting frame 40 by the tissue anchors 34, 36 and only afterwards is the sheath 42 moved into position. The cross-section of the elastomeric sheath 42, shown best in FIG. 9B, is somewhat like an inverted "J" with two rims adjacent to the elastomeric sheath base 44. The elastomeric sheath 42 is designed to be a stretch-fit over the assembled frame structure having the three leaflets 50 attached. When the elastomeric sheath 42 is stretched over the assembled frame structure, the tissue anchors 34 and 36 locate loosely within the Dacron covered elastomeric sheath holes 50, as best shown in FIG. 11B.

The top of the inverted "J" of the outer elastomeric sheath fits over the top of the commissure posts 14 of the frame 40. The tissue leaflets 50 attached to the commissure post anchors 34 and the cusp line hooks 36 and are then held in place between the inner wall of the elastomeric sheath 42 and the tissue mounting frame 40. The elastomeric sheath holes 64 accommodate the hook section of the commissure post anchors 34 and cusp line anchors 36 which protrude beyond the tissue. FIG. 10A shows the commissure post anchors 34 and cusp line anchors 36 fitted into the elastomeric sheath holes 64.

The elastomeric sheath 42 is fixed by its DACRON cover to the base of the frame assembly by thermally welding, suturing, or sewing it to the DACRON cover of the frame assembly. The elastomeric sheath 42 is also held in position on the commissure posts 14 of the frame by an elastomeric sheath pocket 84 situated at the top of the inverted "J" of the outer sheath (FIG. 11B).

Sewing Ring

A DACRON covered sewing ring 70, shown in FIGS. 11A, 11B, 11C and 12A, 12B, is located at the base of the assembled valve. The sewing ring advantageously has a wedge shaped cross-section and is preferably made of silicon rubber, though other materials can be used, provided that they are flexible, resilient, and durable. The sewing ring is thin and flexible so that it can accurately conform to the scalloped shape of the aortic root when the valve is implanted into the patient.

The sewing ring, tissue mounting frame, and elastomeric sheath are joined together by joining all six layers of DACRON together in a thermal weld point 110, shown in FIGS. 11B and 11C. The thermal weld 110 is formed with the sewing ring almost in line with the tissue mounting frame. When the sewing ring is moved into the position shown in FIG. 11B, the weld point is hidden between the sewing ring and the outer sheath. This prevents thromboembolisms from forming on the relatively smooth surface of the weld.

The tissue mounting frame, tissue anchors, and elastomeric sheath comprise a kit which can be preassembled in the factory and shipped for use in an operating room. The kit can be fitted together and the elastomeric sheath aligned with the tissue mounting frame in the factory. Preferably, the tissue mounting frame, and elastomeric sheath are covered with DACRON, and the layers of DACRON are welded together with the thermal weld point 110 shown in FIGS. 11B and 11C, as previously described.

Optionally, the kit can additionally comprise a sewing ring attached to the tissue mounting frame and elastomeric sheath. Preferably, the sewing ring is also covered with DACRON and is attached to the tissue mounting frame and elastomeric sheath by welding the six DACRON layers together in a thermal weld point 110, as previously described.

Preparation of the Autologous Tissue Leaflets 50

The general shape of each tissue leaflet 50 is shown in FIG. 7A. The shape has been designed to form a cusp shape and to minimize tissue stress. The length of tissue along the tissue cusp line 94 is slightly greater than the cusp line length 30 of the tissue frame, as shown in FIG. 2B, so that the extra tissue can form a cup shape, a process not dissimilar from that used to form the bust in ladies dresses. Although there is more tissue than required for the cusp length, it is not sufficient to cause folds or wrinkles in the tissue.

The tissue leaflets are typically cut with a tissue cutting die configured to both the size of the ultimate valve and also to provide for additional tissue on one side of the leaflet. Examples of cutting dies suitable for cutting predetermined shapes in autologous tissue are shown and described in U.S. Pat. Nos. 5,163,955 and 5,425,741. In the preferred embodiment, disposable tissue cutting dies will be supplied and used in a housing which may be non-disposable.

For use in this invention, the cutting die is configured so that the tissue leaflets 50 are cut in a manner to take account of the extra tissue required for the overlap on the commissure posts 14 as shown in FIG. 11B. The radius along the coaptation line of the leaflet whose tissue, at the commissure post, is on top of the adjacent leaflet (leaflet 50a in FIG. 11B) is lengthened by the extra amount needed to overlay the inner leaflet. The tissue cutting die or other cutting device is configured to provide for this extra tissue on one side of the leaflet and also chamfer one corner of the cut leaflet to identify which leaflet is placed on top of the preceding leaflet. The tissue leaflet chamfer 66 is shown in FIG. 7A.

Figure 7B:
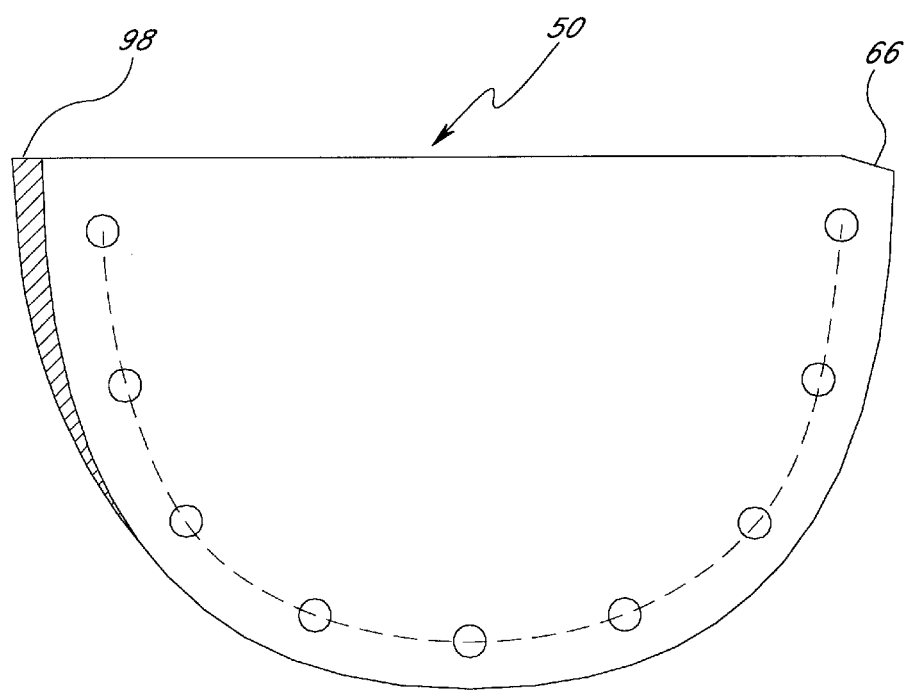
FIG. 7B is a front view of the autologous tissue leaflet of FIG. 7A, showing the excess tissue for overlap of the tissue leaflets on the commissure hooks.

The greater length of the side of the tissue leaflet which is on top is shown in FIG. 10C. The radius along the coaptation line of the leaflet whose tissue is on top of the adjacent leaflet (leaflet 50a in FIG. 11B) is lengthened by the extra amount needed to overlay the inner leaflet. The extra tissue, as measured from the centerline of the tissue leaflet, is shown as the crosshatched area 98 in FIG. 7B.

In addition to the tissue cutting die, other intra-operative techniques can be employed to precisely cut the tissue leaflets, examples being water jet or laser cutting apparatus.

Figure 13:
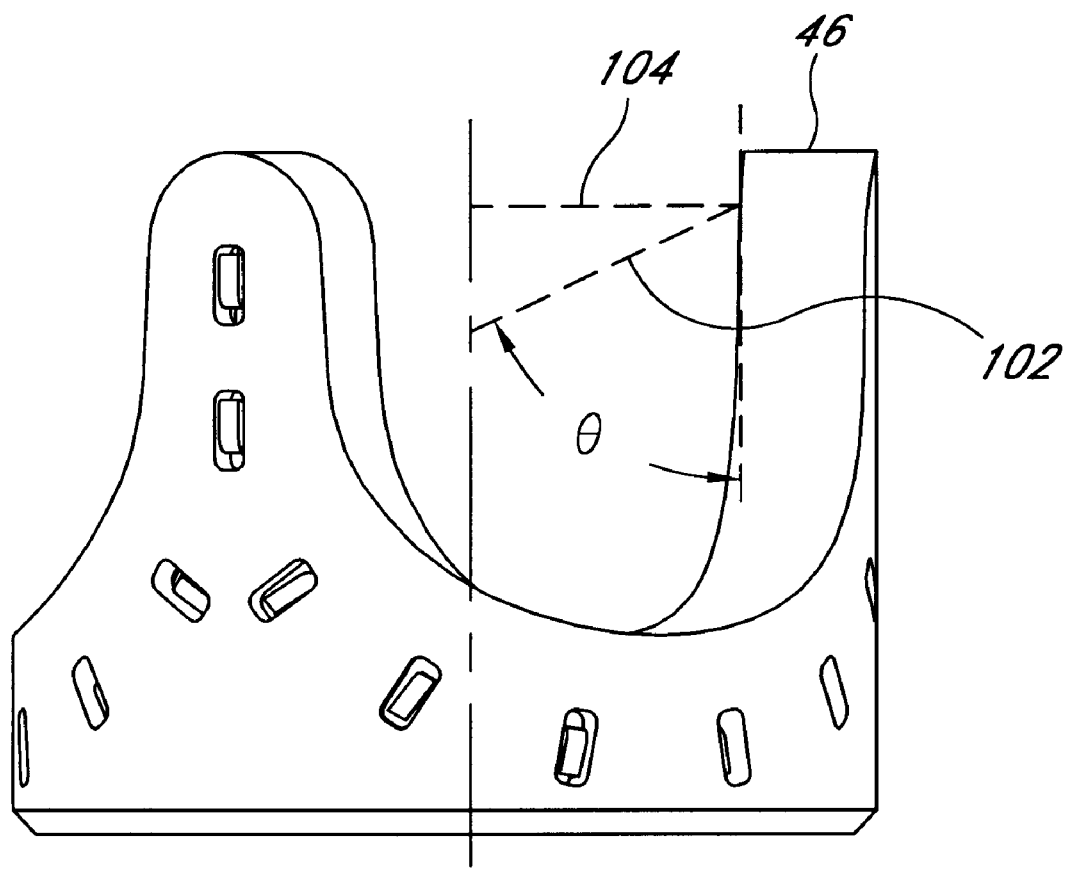
FIG. 13 illustrates the reduced coaptation angle θ of the preferred embodiment of this invention.

A feature of the preferred embodiment of the invention is that it does not require a horizontal coaptation line. As shown in FIG. 13, such a horizontal coaptation line 104 significantly increases the stress in the tissue at the commissure post 14. This is analogous to the tension required to hold a washing line very taut compared to a line which is allowed to have a degree of curvature. In the heart valves constructed according to the preferred embodiment of the present invention, the outer elastomeric sheath 42 holds the tissue leaflets 50a and 50b around the commissure post 14 of the tissue mounting frame 40. The tissue length along the coaptation line is more than twice the radius of the valve. Taking account of tissue stretch, this extra tissue results in a coaptation to commissure post angle of approximately 65 degrees labelled as 102 in FIG. 13. This reduced coaptation angle θ greatly reduces the stress in the tissue leaflets at the commissure post 14.

The tissue for constructing the tissue leaflets 50 is preferably autogenous tissue, such as pericardial tissue, but it may also be fascia lata, rectus fascia, or vein tissue. These tissue sources are all relatively flimsy and difficult to handle. This is because, once harvested, the tissue will have a thickness of about 10–12 mils. By comparison, bovine pericardium is about 15–20 mils thick. After the tissue is harvested, it is usually partially fixed by immersion in 0.625% glutaraldehyde solution for approximately 10 minutes. This both toughens the tissue and makes it easier to handle.

Other tissue sources besides autogenous tissue are, of course, possible, such as bovine pericardium or other xenograft tissue or the like. Further, homograft tissue is possible. These tissues could be pre-cut by the valve builder or manufacturer outside the operating room and stored via conventional methods. If other tissue sources are used, however, the dimensions of the components would be adjusted to accommodate the tissue, which is generally thicker than the preferred tissue sources.

Intraoperative Valve Construction

The cleaning, harvesting, and fixing processes for the autologous tissue are known in the art and described, for example, in U.S. Pat. No. 5,163,955.

Following fixing, the three separate leaflets 50 are cut, as described above.

The three leaflets, the dimensions of which allow for overlap with the cropped corner 66 (FIG. 7A) are placed on top of the preceding leaflets. The leaflets are placed sequentially on the tissue anchor hooks 34, 36 in the cloth covered tissue mounting frame 40.

The elastomeric sheath 42 is then folded or rolled-up over the frame 40 and the mounted tissue leaflets so that the concave pocket 84 situated at the top of each elastomeric sheath commissure post section 46 of the sheath 42 is hooked over a commissure post 14 of the tissue mounting frame 40. In the preferred embodiment, the DACRON covered elastomeric sheath rests gently on the tissue leaflets around the cusp line (see FIG. 11C) such that the tissue leaflets form the naturally closed valve shown in FIG. 1. Sheath 42 prevents the tissue leaflets 50 from coming off the tissue anchor hooks 34, 36, and the sheath substantially encloses and "hugs" the upper portion of the commissure posts 14 and the tissue leaflets attached thereto, as shown in FIG. 10C, so that the adjacent leaflets touch each other in the coaptation line.

The completed valve is tested and then mounted to a holder for implantation in accordance with the teachings of the prior art. See, e.g., U.S. Pat. No. 5,163,955.

What is claimed is:

1. A tissue heart valve comprising:
   (a) a sub-assembly including:
   a tissue mounting frame having a generally cylindrical base, a plurality of commissure posts, and a plurality of outwardly projecting tissue anchors;
   a sewing ring attached to said tissue mounting frame, and
   an elastomeric sheath attached to said tissue mounting frame; and (b) a plurality of tissue leaflets intraoperatively cut and retained by respective tissue anchors so that said tissue leaflets are sequentially located around the circumference of said tissue mounting frame with each leaflet extending from one commissure post to an adjacent commissure post, with said elastomeric sheath (i) resting gently on tissue leaflets to maintain said leaflets to said tissue anchors, and (ii) enclosing the upper portion of said commissure posts and the tissue leaflets attached thereto so that the leaflets form valve cusps, wherein said tissue leaflets are oversized to promote the formation of valve cusps.

2. The tissue heart valve of claim 1, wherein said tissue mounting frame comprises an inner frame secured to an outer frame.

3. The tissue heart valve of claim 1, wherein said tissue leaflets are oversized so that said elastomeric sheath holds said plurality of tissue leaflets together with a physiologically representative coaptation angle of less than 90°.

4. The heart valve of claim 3, wherein said coaptation to commissure post angle is approximately 65°.

5. The heart valve of claim 1, wherein said elastomeric sheath self adjusts to apply equal force to said tissue leaflets on said frame.

6. The heart valve of claim 1, wherein said tissue anchors are hooks and said elastomeric sheath has a plurality of holes accommodating said hooks.

7. The heart valve of claim 6, wherein openings in said elastomeric sheath accommodate the exterior portions of said hooks.

8. The heart valve of claim 1, wherein said elastomeric sheath is factory aligned with said tissue mounting frame.

9. The heart valve of claim 1, wherein the tissue leaflets are supported and retained by the combination of (i) mounting openings in said leaflets respectively mounted on said tissue anchors and (ii) said elastomeric sheath engaging a peripheral portion of said tissue leaflets between said outer elastomeric sheath and said inner tissue mounting frame, without clamping said tissue between two unyielding members.

10. The heart valve of claim 1, wherein said tissue leaflets comprise partially fixed autologous tissue.

11. The heart valve of claim 1, wherein said tissue leaflets comprise partially fixed autologous pericardial tissue.

12. The heart valve of claim 1, wherein said tissue mounting frame is covered with a fabric.

13. A tissue heart valve comprising:

(a) a sub-assembly including:

a tissue mounting frame having a generally cylindrical base, a plurality of commissure posts, and a plurality of outwardly projecting tissue anchors, wherein said tissue mounting frame is covered with a fabric comprising polyethylene terephthalate;

a sewing ring attached to said tissue mounting frame, and an elastomeric sheath attached to said tissue mounting frame; and (b) a plurality of tissue leaflets intraoperatively cut and retained by respective tissue anchors so that said tissue leaflets are sequentially located around the circumference of said tissue mounting frame with each leaflet extending from one commissure post to an adjacent commissure post, with said elastomeric sheath (i) resting gently on tissue leaflets to maintain said leaflets to said tissue anchors, and (ii) enclosing the upper portion of said commissure posts and the tissue leaflets attached thereto so that the leaflets form valve cusps.

14. A heart valve comprising:

a frame comprising an annular base and a plurality of posts extending from said base;

a plurality of tissue anchors attached to said frame;

a plurality of tissue leaflets retained by said tissue anchors, wherein said tissue anchors are hooks and said tissue leaflets are retained on multiple hooks on said frame; and a flexible elastomeric sheath, wherein said sheath fits around said frame and said tissue leaflets and retains said tissue leaflets on said tissue anchors.

15. A heart valve comprising:

a frame comprising an annular base and a plurality of posts extending from said base;

a plurality of tissue anchors attached to said frame;

a plurality of tissue leaflets retained by said tissue anchors, wherein said tissue leaflets are oversized to promote the formation of valve cusps; and a flexible elastomeric sheath, wherein said sheath fits around said frame and said tissue leaflets and retains said tissue leaflets on said tissue anchors.

16. A heart valve comprising:

a frame comprising an annular base and a plurality of posts extending from said base;

a plurality of tissue anchors attached to said frame;

a plurality of tissue leaflets retained by said tissue anchors; and a flexible elastomeric sheath, wherein said sheath fits around said frame and said tissue leaflets and retains said tissue leaflets on said tissue anchors, wherein said elastomeric sheath holds said plurality of tissue leaflets together at a coaptation angle less than 90°.

17. The heart valve of claim 14, wherein said elastomeric sheath has a plurality of holes accommodating said hooks.

18. A heart valve comprising:

a frame comprising an annular base and a plurality of posts extending from said base, wherein said frame is covered with a fabric comprising polyethylene terephthalate;

a plurality of tissue anchors attached to said frame;

a plurality of tissue leaflets retained by said tissue anchors; and a flexible elastomeric sheath, wherein said sheath fits around said frame and said tissue leaflets and retains said tissue leaflets on said tissue anchors.

19. The heart valve of claim 15, wherein said tissue leaflets comprise autologous tissue.

20. The heart valve of claim 19, wherein said autologous tissue is partially fixed.

21. The heart valve of claim 19, wherein said autologous tissue is unfixed.

22. The heart valve of claim 19, wherein said autologous tissue leaflets comprise bovine tissue.

* * * * *